United States Patent [19]

Wettermann

[11] Patent Number: 5,183,470
[45] Date of Patent: Feb. 2, 1993

[54] LAPAROSCOPIC CHOLANGIOGRAM CATHETER AND METHOD OF USING SAME

[75] Inventor: Peter H. Wettermann, Pomfret, Conn.

[73] Assignee: International Medical, Inc., Danielson, Conn.

[21] Appl. No.: 664,373

[22] Filed: Mar. 4, 1991

[51] Int. Cl.$^5$ ............................................. A61M 25/00
[52] U.S. Cl. .................................. 604/281; 604/264; 604/158; 604/170
[58] Field of Search .................................. 604/158–170, 604/281, 283, 49, 53, 96, 101, 264, 280; 128/656–658, 4; 606/194

[56] References Cited

U.S. PATENT DOCUMENTS

| | | |
|---|---|---|
| 3,399,668 | 9/1968 | Lundgren . |
| 3,856,009 | 12/1974 | Winnie ................................. 604/164 |
| 3,918,456 | 11/1975 | Patel . |
| 4,044,757 | 8/1977 | McWhorter et al. . |
| 4,044,758 | 8/1977 | Patel . |
| 4,263,917 | 4/1981 | Moss . |
| 4,306,566 | 12/1981 | Sinko . |
| 4,447,236 | 5/1984 | Quinn .................................. 604/169 |
| 4,512,765 | 4/1985 | Muto .................................. 604/281 |
| 4,553,960 | 11/1985 | Lazarus et al. ....................... 604/158 |
| 4,581,017 | 4/1986 | Sahota ................................. 604/101 |
| 4,582,181 | 4/1986 | Samson ................................ 606/194 |
| 4,734,094 | 3/1988 | Jacob et al. . |
| 4,738,658 | 4/1988 | Magro et al. . |
| 4,738,667 | 4/1988 | Galloway ............................. 604/281 |
| 4,747,823 | 5/1988 | Buchanan . |
| 4,792,330 | 12/1988 | Lazarus et al. . |
| 4,807,626 | 2/1989 | McGirr ................................ 604/281 |
| 4,838,829 | 6/1989 | Tanabe et al. . |
| 4,846,799 | 7/1989 | Tanaka et al. ....................... 604/158 |
| 4,905,667 | 3/1990 | Foerster et al. ...................... 604/280 |
| 4,919,651 | 4/1990 | Doane . |
| 4,935,017 | 6/1990 | Sylvanowicz ......................... 604/281 |
| 4,969,875 | 11/1990 | Ichikawa ............................. 604/164 |
| 4,973,312 | 11/1990 | Andrew ............................... 604/158 |
| 4,986,814 | 1/1991 | Burney et al. ....................... 604/164 |
| 4,994,032 | 2/1991 | Sugiyama et al. .................... 606/194 |

Primary Examiner—Stephen C. Pellegrino
Assistant Examiner—Ralph A. Lewis
Attorney, Agent, or Firm—Samuels, Gauthier & Stevens

[57] ABSTRACT

A cholangiogram catheter for use in a laparoscopic cholecystectomy has a rigid tubular outer sheath dimensioned to slide within an associated trocar sleeve, and an outer tubular catheter is slidably seated within the outer sheath with its distal end portion formed into a 90° bend and is resiliently deflectable for withdrawal into the sheath. A flexible inner tubular catheter is readily slidable within the outer catheter and is longitudinally dimensioned to extend outwardly of both ends of the outer catheter. The distal end of the inner catheter has a closed tip and a discharge aperture along its side adjacent the tip. Luer connectors are attached to the proximal ends of the several elements.

7 Claims, 1 Drawing Sheet

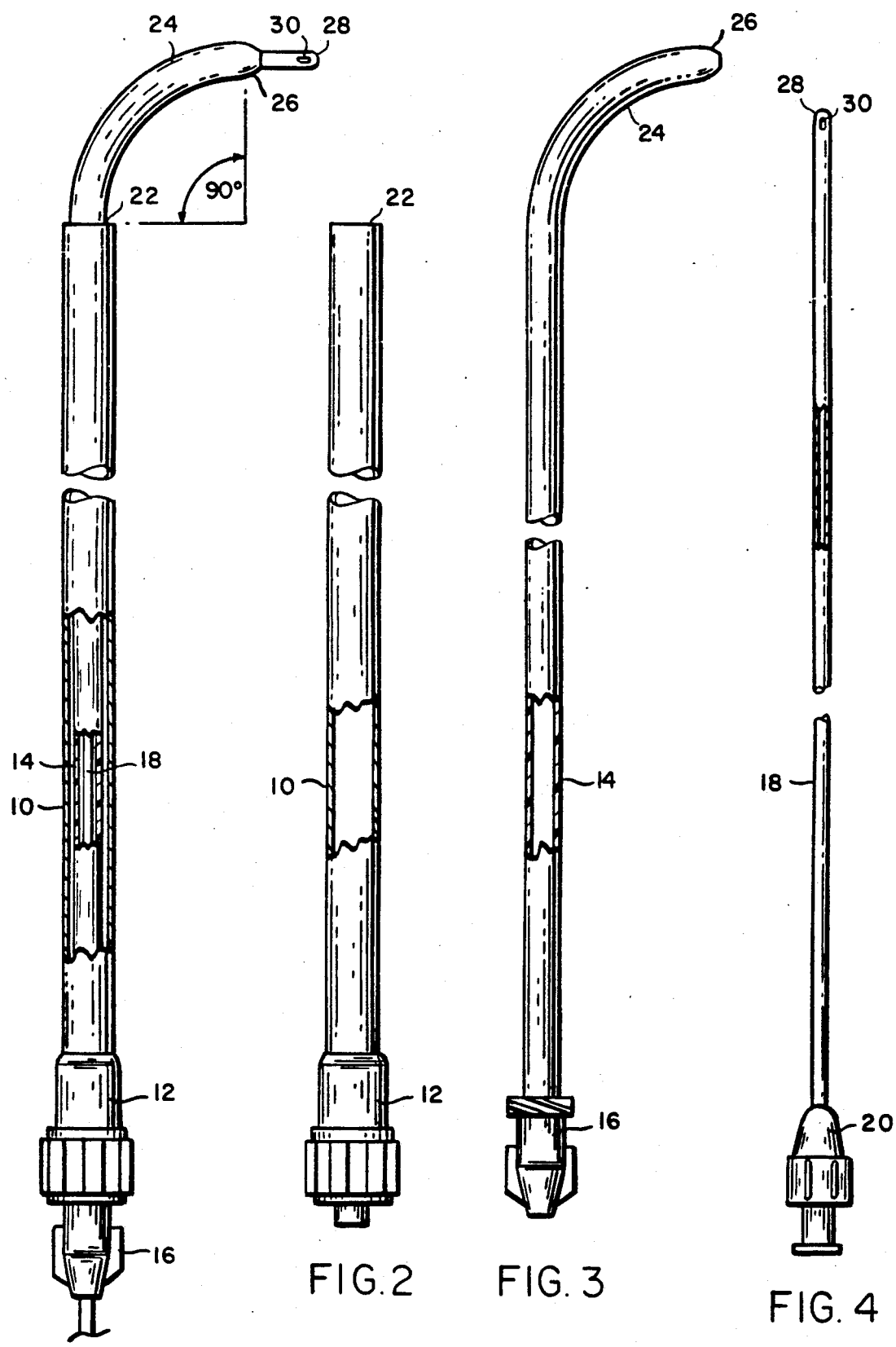

LAPAROSCOPIC CHOLANGIOGRAM CATHETER AND METHOD OF USING SAME

BACKGROUND OF THE INVENTION

The present invention relates to catheters and, more particularly, to a cholangiogram catheter and the method of using the same.

Recently, a new surgical technique has been developed whereby the gall bladder is surgically removed by use of a telescopic device called a laparoscope. This procedure is called a laparoscopic cholecystectomy and is performed by making a tiny incision at the umbilicus and inserting the telescopic device to which a small video camera is attached. By utilizing several monitors, the surgeons are able to view the abdominal cavity as the distal end of the telescopic device is moved thereabout.

Three other small incisions are made through which various grasping and cutting forceps are inserted, and these are used to grasp and manipulate the gall bladder so as to separate it from the liver bed. Once the gall bladder is detached from the liver bed, it is pulled through one of the small incisions. Prior to resecting the gall bladder from the liver, the surgeon determines whether the patient has stones in the common duct and at the cystic-common duct junction. This is done with a procedure called a cholangiogram.

In open cholecystectomies (i.e., where a relatively large incision is made in the abdominal wall), the surgeon transects the cystic duct to its midline and with a curved forceps introduces an acorn-tipped catheter into the opening. The concept of the acorn is to plug the incision so that when a dye is injected through the catheter, it does not leak out. Once a good flow of dye is established, an X-ray is taken to determine whether any common duct stones are present. Unfortunately, the acorn-tipped catheter will slide only into large cystic ducts.

Using such an acorn-tipped catheter in laparoscopic cholecystectomies is even more difficult. Once the surgeon has transected the cystic duct to its midline with a pair of microscissors, the acorn-tipped catheter is inserted through one of the small incisions. Because the body of the catheter is plastic and about 2 mm in diameter, it must be held near the top with a pair of grasping forceps which are inserted through another incision. Due to the locations of the incisions, the acorn-tipped catheter approaches the transected duct at a 90° angle. In order to push the tip of the catheter into the opening and to slide it into the lumen toward the common duct, it must be deflected 90°. This is difficult to do, especially when the inner lumen is small.

It is an object of the present invention to provide a novel cholangiogram catheter which may be easily manipulated for laparoscopic cholangiograms.

It is also an object to provide such a cholangiogram catheter which is dimensioned to fit through a standard 5.5. mm trocar sleeve typically used in a laparoscopic cholecystectomy.

Another object is to provide such a cholangiogram catheter which, after insertion into the abdominal cavity, may be deflected 90° so that it may be inserted in a direction parallel to the cystic duct.

Another object is to provide such a cholangiogram catheter which includes a small inner catheter which will slide easily into the lumen of the cystic duct and an outer catheter with a tapered tip which slides over the inner catheter and occludes the transected duct to prevent the backflow of dye.

SUMMARY OF THE INVENTION

It has now been found that the foregoing and related objects may be readily attained in a cholangiogram catheter which include a rigid tubular outer sheath dimensioned to slide within an associated trocar sleeve and a luer connector attached to the distal end of the sheath. Slidably seated within the outer sheath is an outer tubular catheter longitudinally dimensioned to extend outwardly of both ends of the sheath. The outer catheter has its distal end portion formed into a 90° bend and is resiliently deflectable for withdrawal into the sheath. A luer connector is attached to the proximal end of the outer catheter, and it is engageable with the connector of the outer sheath.

Readily slidable within the outer catheter is a flexible inner tubular catheter and it is longitudinally dimensioned to extend outwardly of both ends of the outer catheter. The distal end of the inner catheter has a closed tip and a discharge aperture along its side adjacent the tip. Lastly, a luer syringe connector is attached to the proximal end of the inner catheter.

In a preferred embodiment, the outer sheath is metallic and has a chamfered or rounded distal end, and the outer catheter is formed from synthetic resin with a tapered tip. The closed tip at the distal end of the inner catheter is also tapered in a bullet shape.

In the method for using this cholangiogram catheter for insertion into the cystic duct of the patient, the luer connector of the outer connector is disengaged from the luer connector of the outer sheath, and the outer catheter is pulled proximally until the bent portion of the outer catheter is withdrawn within the outer sheath. The outer sheath is slid through a trocar sleeve into the abdominal cavity, and the outer catheter is pushed inwardly of the outer sheath until the luer connector thereon engages with the connector of the outer sheath. At this point, the distal end portion of the outer catheter projects outwardly of the distal end of the sheath and resumes its 90° bend.

The inner catheter is pushed through the outer catheter until its distal tip extends approximately 1 cm beyond the distal tip of the outer catheter, and the outer sheath is manipulated to position the bent portion of the outer catheter and the extending distal end of the inner catheter parallel to the cystic duct. The distal end of the inner catheter is then inserted into the cystic duct, and the outer catheter is advanced over the distal end portion of the inner catheter until its distal end portion is wedged into the opening of the cystic duct to prevent backflow of contrast material.

The method also includes the additional steps of connecting a syringe to the luer syringe connector of the inner catheter and injecting a contrast material into the cystic duct.

BRIEF DESCRIPTION OF THE DRAWINGS

FIG. 1 is a fragmentary view of a cholangiogram catheter embodying the invention with portions of the outer sheath and of the outer catheter broken away;

FIG. 2 is a fragmentary view of the outer sheath and its male luer connector and with a portion of the sheath broken away;

FIG. 3 is a fragmentary view of the outer catheter and its female luer connector with a portion of the catheter broken away; and FIG. 4 is a fragmentary view of the inner catheter with its luer syringe connector and with a portion of the catheter broken away.

DETAILED DESCRIPTION OF PREFERRED EMBODIMENT OF THE INVENTION

Turning first to FIG. 1, a cholangiogram catheter 10 embodying the present invention is comprised of three principal components: a rigid outer sheath generally designated by the numeral 10 having a male luer connector 12 attached to its proximal end, an outer catheter generally designated by the numeral 14 slidably seated in the outer sheath 10 and having a female luer connector 16 attached to its proximal end, and an inner catheter generally designated by the numeral 18 which is slidably seated in the outer catheter 14 and which has a luer syringe connector 20 attached to its proximal end.

As seen in FIG. 2, the distal end 22 of the sheath 10 is rounded or chamfered. As seen in FIGS. 1 and 3, the end portion 24 of the outer catheter 14 is arcuately curved to terminate at a 90° angle to the longitudinal axis of the outer sheath 10, and it has a tip 26 which is tapered. As seen in FIGS. 1 and 4, the distal end of the inner catheter 18 is closed with a bullet shaped tip 28, and it has an oval aperture 30 along one side thereof inwardly of the end of the tip 28.

In the use of the cholangiogram catheter of the present invention, a trocar sleeve (not shown) is inserted through an incision and used for placement of the catheter. Prior to insertion, the female luer connector 16 of the outer catheter 14 is unlocked from the male luer connector 12 of the outer sheath 10. The luer connector 16 is then pulled proximally until the curved end portion 24 of the outer catheter 14 is drawn into the outer sheath 10. The outer sheath 10 can now be inserted through the trocar sleeve (not shown). Once the distal end of the outer sheath 10 is disposed in its desired position inside the abdominal cavity (not shown), the female luer connector 16 is pushed forwardly, causing the distal end portion 24 of the outer catheter 14 to extend from the distal end of the outer sheath 10 and resume its original 90° arc. The female luer connector 16 is then locked into the male luer connector 12 of the outer sheath 10.

The inner catheter 18 is pushed forwardly until its distal end extends about 1 cm beyond the distal end of the outer catheter 14. The sheath 10 is positioned so that the tip 26 of the outer catheter 14 is parallel to the cystic duct (not shown), and the tip 28 of the inner catheter 18 is pushed into the lumen of the cystic duct for a distance of approximately 1 cm. The outer catheter 14 is then advanced along the inner catheter 18 until its tapered tip 26 is inside the lumen of the cystic duct. This will prevent any backflow of contrast material.

A syringe (not shown) may now be attached to the luer syringe connector 20 of the catheter 18, and a contrast material is injected through the inner catheter 18 into the cystic duct. An X-ray may then be taken to determine if there are any gall stones in the common and cystic ducts.

As will be appreciated, the outer catheter must be formed from a material which can be performed with a 90° bend at its distal end and which is resiliently deflectable so that the arcuate or bent end portion may be straightened as it is withdrawn into the outer sheath and so that it will recover into its bent form upon extension therefrom. Although a spring tempered metal tube might be employed, synthetic resins are preferred for this member, and polyurethane tubing has been found quite satisfactory. The 90° bend is conveniently effected with this resin by heating it to about 200°–250° F., placing the end portion on a mandrel with the desired curvature and cooling it to room temperature on the mandrel.

Although the outer sheath may be formed of synthetic resin, stainless steel tubing is preferred because the necessary rigidity may be obtained with a relatively small wall thickness. Desirably, the distal end should be ground or machined to provide a rounded or tapered end.

The inner catheter is fabricated from thin walled synthetic resin tubing. Although various resins may be employed, care should be used to select a resin which is inert to the dye and which exhibits a high degree of flexure so as to readily move through the outer catheter and the cystic duct. Nylon tubing has been found highly satisfactory.

The luer connectors are conventional and may be secured to the synthetic resin catheters by heat sealing or adhesive. The connector may be secured to the metallic outer sheath by an adhesive.

The following is a specific example of a highly satisfactory cholangiogram catheter embodying the present invention for use with a trocar sleeve of 5.5 mm diameter:

Stainless Steel Outer Sheath: 0.188 inch O.D., 0.140 inch I.D., 9.0 inches long;

Outer Polyurethane Catheter: 0.115 inch O.D., 0.140 inch I.D., 12 inches long, with 90° arc beginning 1.25 inches from distal end;

Inner Nylon Catheter: 0.061 inch O.D., 0.031 inch I.D., 30 inches long.

Although the cholangiogram catheter of the present invention is primarily for the purpose of injecting a contrast material through the inner catheter, other elements may also be inserted through the outer catheter. Because the outer catheter has a distal end portion which deflects at 90°, it may be used to insert a laser fiber or a flexible, high frequency coagulation electrode through the outer catheter to achieve a better cutting angle.

Thus, it can be seen from the foregoing detailed specification and claims that the cholangiogram catheter of the present invention is one which enables facile placement in the abdominal cavity and parallel orientation of the dye injecting catheter element for insertion into the cystic duct. Its components are readily fabricated and assembled to provide an assembly which may be manipulated easily, and the catheter occludes the cystic duct to prevent backflow of the dye which is inserted therethrough.

Having thus described the invention, what is claimed is:

1. A cholangiogram catheter comprising:
   (a) a rigid tubular outer sheath having a distal end and a proximal end;
   (b) a first luer connector attached to the proximal end of said sheath;
   (c) an outer tubular catheter slidably seated within said outer sheath and having a proximal end and a distal portion;
   (d) a second luer connector attached to the proximal end of said outer catheter, said second connector having means engageable with the first connector to releasably fix said outer tubular catheter in relation to said sheath, said distal end portion protruding form the distal end of said outer sheath as a permanently preformed arcuate resilient curve when said second connector engaged with said first connector;

(e) a flexible inner tubular catheter readily slidable within said outer catheter and longitudinally dimensioned to extend outwardly of both ends of said outer catheter, the distal end of said inner catheter having a closed tip and a discharge aperture; and (f) a third luer connector attached to the proximal end of said inner catheter for connecting said inner catheter to an injection device.

2. The cholangiogram catheter in accordance with claim 1 wherein said outer catheter is formed from synthetic resin.

3. The cholangiogram catheter in accordance with claim 1 wherein said distal end portion of said outer catheter has a tapered tip.

4. The cholangiogram catheter in accordance with claim 1 wherein said outer sheath is metallic and has a chamfered distal end.

5. The cholangiogram catheter in accordance with claim 1, wherein the discharge aperture of said inner catheter is positioned adjacent to said closed tip.

6. In a method for inserting a cholangiogram catheter into a cystic duct of a patient, the steps comprising:

(a) disengaging a first luer connector attached to the proximal end of a rigid tubular outer sheath, from a second luer connector attached to the proximal end of an outer catheter having its distal end portion formed into an arcuate curve and being resiliently deflectable for withdrawal into said sheath;

(b) pulling said outer catheter proximally until said curved portion of said outer catheter is withdrawn within said outer sheath;

(c) sliding said outer sheath through a trocar sleeve into an abdominal cavity;

(d) pushing said outer catheter inwardly of said outer sheath until said second luer connector thereon engages with said first luer connector, and said distal end portion of said outer catheter projects outwardly of the distal end of said sheath and resumes its arcuate curve;

(e) pushing a flexible inner tubular catheter, having a luer connector attached to the proximal end, through said outer catheter until the distal end, having a closed tip and a discharge aperture along its side adjacent said tip, extends beyond the distal tip of said outer catheter;

(f) manipulating said outer sheath to position said curved portion of said outer catheter and the extending distal end of said inner catheter parallel to the cystic duct;

(g) inserting the distal end of said inner catheter into said cystic duct; and (h) advancing said outer catheter over the distal end portion of said inner catheter until its distal end portion is wedged into the opening of the cystic duct to prevent back-flow of contrast material.

7. The method of inserting a cholangiogram catheter in accordance with claim 6 including the additional steps of connecting a syringe to the third luer connector of said inner catheter and injecting a contrast material into the cystic duct.

* * * * *